US009211262B2

(12) United States Patent
Bernareggi et al.

(10) Patent No.: US 9,211,262 B2
(45) Date of Patent: Dec. 15, 2015

(54) INJECTABLE PHARMACEUTICAL COMPOSITIONS OF AN ANTHRACENEDIONE DERIVATIVE WITH ANTI-TUMORAL ACTIVITY

(75) Inventors: Alberto Bernareggi, Concorezzo (IT); Valeria Livi, Monza (IT)

(73) Assignee: CTI BioPharma Corp., Seattle, WA (US)

( * ) Notice: Subject to any disclaimer, the term of this patent is extended or adjusted under 35 U.S.C. 154(b) by 458 days.

(21) Appl. No.: 12/964,861

(22) Filed: Dec. 10, 2010

(65) Prior Publication Data

US 2011/0144147 A1    Jun. 16, 2011

Related U.S. Application Data

(63) Continuation of application No. 10/514,301, filed as application No. PCT/EP03/04871 on May 9, 2003, now abandoned.

(30) Foreign Application Priority Data

May 16, 2002    (IT) .............................. MI2002A1040

(51) Int. Cl.
| A61K 9/19 | (2006.01) |
| A61K 9/00 | (2006.01) |
| A61K 47/02 | (2006.01) |
| A61K 47/26 | (2006.01) |
| A61K 47/36 | (2006.01) |

(52) U.S. Cl.
CPC ................ *A61K 9/19* (2013.01); *A61K 9/0019* (2013.01); *A61K 47/02* (2013.01); *A61K 47/26* (2013.01); *A61K 47/36* (2013.01)

(58) Field of Classification Search
CPC ................................ A61K 9/19; C07D 221/08
See application file for complete search history.

(56) References Cited

U.S. PATENT DOCUMENTS

| 3,590,124 A | 6/1971 | Hoyt | |
| 4,822,785 A | * 4/1989 | Ishibashi et al. | ............... 514/202 |
| 5,587,382 A | * 12/1996 | Krapcho et al. | ............... 514/290 |

FOREIGN PATENT DOCUMENTS

| EP | 0 503 537 A1 | 9/1992 |
| JP | 8-126685 A | 5/1996 |
| WO | 01/28521 A2 | 4/2001 |

OTHER PUBLICATIONS

Magni et al 'Identification of two novel impurities during the development of an aza-athracenedione drug' Journal de Pharmacie de Belgique, 53(3), p. 217, abstract, 1998.*
Nema et al 'Excipients and Their Use in Injectable Products' PDA Journal of Pharmaceutical Science and Technology, 51(4), p. 166-171, 1997.*
Akers, "Excipient-Drug Interactions in Parenteral Formulations," *Journal of Pharmaceutical Sciences* 91(11):2283-2300, 2002.
Magni et al., "Indentification of two novel impurities during the development of an aza-anthracenedione drug," *Journal de Pharmacie de Belgique* 53(3):217, 1998, Abstract only.
Nema et al., "Excipients and Their Use in Injectable Products," *PDA J Pharm Sci and Tech* 51:166-171, 1997.
Bharate et al., "Interactions and incompatibilities of pharmaceutical excipients with active pharmaceutical ingredients: a comprehensive review." *J. Excipients and Food Chem.* 1(3):3-26, 2010.
Wirth et al., "Maillard Reaction of Lactose and Fluoxetine Hydrochloride, a Secondary Amine," *Journal of Pharmaceutical Sciences* 87(1):31-39, 1998.

* cited by examiner

*Primary Examiner* — Wu-Cheng Winston Shen
*Assistant Examiner* — Christopher R Stone
(74) *Attorney, Agent, or Firm* — Seed IP Law Group PLLC

(57) ABSTRACT

Injectable pharmaceutical compositions containing 6,9-bis [(2-aminoethyl)amino]benzo[g]isoquinoline-5,10-dione dimaleate as active ingredient in the form of a lyophilized powder with a carrier selected from lactose and dextran, mixed with sodium chloride.

9 Claims, No Drawings

INJECTABLE PHARMACEUTICAL COMPOSITIONS OF AN ANTHRACENEDIONE DERIVATIVE WITH ANTI-TUMORAL ACTIVITY

CROSS-REFERENCE TO RELATED APPLICATIONS

This application Ser. No. 12/964,861, filed Dec. 10, 2010, is a Continuation of U.S. patent application Ser. No. 10/514, 301, filed Jul. 18, 2005, now abandoned, which is a National Stage of International Patent Application No. PCT/EP03/04871, filed May 9, 2003, which claims priority from Italian Patent Application No. MI2002A001040, filed May 16, 2002, the disclosures of which are incorporated by reference herein.

The present invention relates to injectable pharmaceutical compositions containing 6,9-bis[(2-aminoethyl)amino]benzo[g]isoquinoline-5,10-dione dimaleate (from now on also referred to as "BBR 2778") as active ingredient in the form of a lyophilised powder with a carrier selected from lactose and dextran, mixed with sodium chloride.

PRIOR ART

BBR 2778 is a novel anthracenedione derivative with anti-tumoral activity which acts as a DNA intercalating agent and topoisomerase II inhibitor. Pre-clinical studies demonstrate that its cardiotoxicity is lower than that of other known drugs belonging to the same class. BBR 2778 has proved more active than mitoxantrone against haematological tumours, especially ascitic L1210 leukaemia and YC-8 lymphoma, in a wide range of doses.

Clinical trials on the use of BBR 2778 in the treatment of non-Hodgkin's lymphoma are at an advanced stage.

The formulation of BBR2778 in injectable liquid pharmaceutical compositions has proved problematic in terms of stability in solution using common solvents suitable for parenteral administration, especially intravenous administration.

A lyophilised formulation to be reconstituted with a suitable solvent such as saline immediately before use has therefore been considered.

Here again, however, unforeseeable problems arose, partly due to the low solubility of BBR 2778 in water and the need to use sodium chloride solutions in concentrations ranging from 0.9 to 4%, in which the drug is progressively more soluble. However, the presence of sodium chloride requires the use of long lyophilisation cycles due to the low glass transition temperature observed.

The choice of lyophilisation carrier has also proved critical in terms of the stability of the final formulation and in operational terms.

For example, if mannitol is used as lyophilisation carrier, stable formulations are only obtained if they are stored at temperatures of approx. 5° C. or lower; stability studies conducted at 25° C. with 60% relative humidity (RH) showed unacceptable levels of degradation products after only one month. The characterisation of the finished product in the solid state demonstrates that BBR 2778 is transformed from a crystalline raw material to an amorphous powder in the lyophilisate, with a consequent reduction in stability. The choice of carriers with greater protective properties consequently focused on polymeric substances like polyvinylpyrrolidone (PVP, Povidone).

Replacing mannitol with Povidone K 17 produced a stable lyophilisate even at 25° C., 60% RH, but Povidone has been removed from the list of excipients approved for parenteral administration in the USA (Fed. Reg. 8 Mar. 1999, Vol. 64, Num. 64) and requires a long lyophilisation cycle due to the low glass transition temperature observed (−37° C.), which requires primary drying to be conducted at a temperature below −37° C.

Unsatisfactory results were also obtained with the use of other conventional lyophilisation carriers such as urea, glycine, ammonium chloride and TRIS in the presence and absence of sodium chloride, and by lyophilisation of BBR 2778 in the absence of excipients.

DESCRIPTION OF THE INVENTION

It has now been found that it is possible to obtain stable lyophilised formulations of BBR 2778 in the presence of sodium chloride by using lactose or dextran as lyophilisation carrier.

A first aspect of the invention therefore provides injectable pharmaceutical compositions containing 6,9-bis[(2-aminoethyl)amino]benzo[g]isoquinoline-5,10-dione dimaleate (BBR 2778) as active ingredient in the form of a lyophilised powder with a carrier selected from lactose and dextran, mixed with sodium chloride, to be reconstituted with a solvent suitable for reconstituting the lyophilisate and suitable for parenteral administration, which solvent is preferably contained in a separate ampoule.

A further aspect of the invention relates to a process for the preparation of said compositions.

DETAILED DESCRIPTION OF THE INVENTION

In the compositions of the invention, the weight ratio between the carrier and sodium chloride is critical, and is typically between 1:1 and 3:1.

The weight ratio between BBR 2778 and the carrier is preferably between 1:2 and 1:6. The particularly preferred carrier is lactose.

The unit dose of BBR 2778 will usually be between 25 and 200 mg, and preferably between 50 and 100 mg. The unit dose currently being tested in clinical trials is 50 mg. For this latter quantity of active ingredient, the preferred compositions according to the invention will contain 100 to 200 mg of sodium chloride and 100 to 300 mg of lactose.

If required, the compositions of the invention can also contain other excipients commonly used for parenteral formulations, such as antioxidants, buffers, local anaesthetics, salts, amino acids and the like.

The vials or ampoules of sterile lyophilised powder will then be reconstituted at the time of use with sterile solvents constituted by sterile pyrogen-free water or sterile saline, in volumes of approx. 5 ml to 20 ml, depending on the active ingredient content.

The compositions of the invention are prepared by a process which comprises lyophilisation of an aqueous solution of BBR 2778, lactose or dextran and sodium chloride by means of:

- a freezing stage at a temperature below at least −45° C. for at least 3 hours;
- a primary drying stage consisting of increasing the temperature of the product to −35° C.±5° C. in approx. 3 hours and maintaining said temperature for at least 40 hours;
- a secondary drying stage consisting of increasing the temperature of the product to +30° C.±5° C. in 10 hours and maintaining said temperature for at least 8 hours.

The compositions according to the invention are stable at room temperature for at least 24 months. The lyophilised product is not subject to deliquescence, and maintains its appearance unchanged over time.

A further advantage of the invention is the reduction in lyophilisation times and the consequent reduction in the cost of the process.

The following examples illustrate the invention in greater detail.

EXAMPLE 1

Preparation of vials containing lyophilised BBR 2778 in the presence of lactose and sodium chloride.

A solution containing 10 mg/ml of BBR 2778, 20 mg/ml of NaCl and 60 mg/ml of lactose, prepared by dissolving the various components in water for injection at 20-25° C., is distributed between type I glass vials under sterile conditions at the rate of 5 ml per vial, after sterile filtration. A lyophilisation stopper is placed on the mouth of the vials.

The pre-stoppered vials are then loaded directly onto lyophilisation shelves and frozen at −45° C.±5° C. for at least 3 hours.

Primary drying is conducted by increasing the temperature of the shelves in the vacuum freeze-dryer from −45° C. to −30° C.±3° C. in 3 hours, and maintaining the temperature at −30° C. for 40 hours.

Secondary drying is performed by increasing the temperature of the shelves from −30° C. to +30° C.±3° C. in 10 hours and then maintaining said temperature of +30° C. for a further 8 hours. The freeze-dryer is returned to atmospheric pressure with nitrogen filtered under sterile conditions, and the vials are stoppered by activating the stoppering device. The vials are unloaded in a sterile environment and crimped.

When reconstituted with 5 ml of water for injection, the solution has a pH of between 3.0 and 4.5.

Accelerated stability tests conducted on the lyophilisate at 40° C. for 12 months have demonstrated a reduction in BBR 2778 titre within the limits of the specifications approved for the product, and a purity exceeding 95%. The stability is also confirmed at 25° C. even after the 12-month observation period.

EXAMPLE 2

Preparation of vials containing lyophilised BBR 2778 in the presence of dextran and sodium chloride.

A solution containing 10 mg/ml of BBR 2778, 20 mg/ml of NaCl and 60 mg/ml of dextran 40000, prepared by dissolving the various components in water for injection at 20-25° C., is distributed between type I glass vials under sterile conditions, at the rate of 5 ml per vial, after sterile filtration. A lyophilisation stopper is placed on the mouth of the vials.

The pre-stoppered vials are then loaded onto trays, which are placed on the shelves of the freeze-dryer. The vials are then frozen in the lyophilisation chamber at −45° C.±5° C. for at least 3 hours.

Primary drying is conducted by increasing the temperature of the shelves in the vacuum freeze dryer from −45° C. to 0° C.±2° C. in 6 hours and maintaining the temperature at 0° C. for 30 hours. The temperature of the product during primary drying is maintained at around −30° C.

Secondary drying is performed by increasing the temperature of the shelves from 0° C. to +30° C.±2° C. in 3 hours and then maintaining said temperature of +30° C. for a further 8 hours. The freeze-dryer is returned to atmospheric pressure with nitrogen filtered under sterile conditions, and the vials are stoppered by activating the stoppering device. The vials are unloaded in a sterile environment and crimped.

When reconstituted with 5 ml of water for injection, the solution has a pH of between 3.0 and 4.5.

Accelerated stability tests conducted on the lyophilisate at 40° C. for 4 months have demonstrated a reduction in BBR 2778 titre within the limits of the specifications approved for the product, and a purity exceeding 96%.

The invention claimed is:

1. A pharmaceutical composition, comprising 6,9-bis[(2-aminoethyl)amino]benzo[g]isoquinoline-5,10-dione dimaleate and a lactose carrier mixed with sodium chloride, wherein the weight ratio between the carrier and sodium chloride is between 1:1 and 3:1,
and wherein the composition is in lyophilized form.

2. The composition according to claim 1, further comprising an antioxidant.

3. The composition according to claim 1, wherein the weight ratio between 6,9-bis[(2-aminoethyl)amino]benzo[g]isoquinoline-5,10-dione dimaleate and the carrier is between 1:2 and 1:6.

4. The composition according to claim 1, wherein 6,9-bis[(2-aminoethyl)amino]benzo[g]isoquinoline-5,10-dione dimaleate is in a unit dose of between 25 and 200 mg.

5. The composition according to claim 4, wherein the unit dose of 6,9-bis[(2-aminoethyl)amino]benzo[g]isoquinoline-5,10-dione dimaleate is 50 mg.

6. The composition according to claim 1, further comprising a sterile solvent suitable to reconstitute the lyophilisate and suitable for parenteral administration.

7. A process for preparing the composition according to claim 1, the process comprising:
lyophilizing an aqueous solution of 6,9-bis[(2-aminoethyl)amino]benzo[g]isoquinoline-5,10-dione dimaleate in the presence of lactose and sodium chloride wherein the step of lyophilizing comprises:
freezing the solution at a temperature below at least −45° C. for at least 3 hours;
drying the frozen solution to form a product, by increasing the temperature of the frozen solution to −35° C.±5° C. in approximately 3 hours and maintaining said temperature for at least 40 hours; and
then drying the product by increasing the temperature of the product to +30° C.±5° C. in 10 hours and maintaining said temperature for at least 8 hours.

8. A composition, comprising an aqueous solution comprising 6,9-bis[(2-aminoethyl)amino]benzo[g]isoquinoline-5,10-dione dimaleate and a) a lactose carrier mixed with sodium chloride, wherein the concentration of 6,9-bis[(2-aminoethyl)amino]benzo[g]isoquinoline-5,10-dione dimaleate is 7-15 mg/ml, and wherein the weight ratio between the lactose carrier and sodium chloride is between 1:1 and 3:1.

9. The composition according to claim 8, comprising 10 to 40 mg/ml of sodium chloride and 20 to 60 mg/ml of lactose.

* * * * *